US012690797B2

(12) United States Patent
Mahajan et al.

(10) Patent No.: US 12,690,797 B2
(45) Date of Patent: Jul. 28, 2026

(54) AMBULATORY DETECTION OF QT PROLONGATION

(71) Applicant: Cardiac Pacemakers, Inc., St. Paul, MN (US)

(72) Inventors: Deepa Mahajan, North Oaks, MN (US); David L. Perschbacher, Blaine, MN (US); Sunipa Saha, Shoreview, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 937 days.

(21) Appl. No.: 17/948,049

(22) Filed: Sep. 19, 2022

(65) Prior Publication Data

US 2023/0107996 A1 Apr. 6, 2023

Related U.S. Application Data

(60) Provisional application No. 63/252,846, filed on Oct. 6, 2021.

(51) Int. Cl.
*A61B 5/06* (2006.01)
*A61B 5/00* (2006.01)
(Continued)

(52) U.S. Cl.
CPC ................ *A61B 5/36* (2021.01); *A61B 5/287* (2021.01); *A61B 5/7475* (2013.01)

(58) Field of Classification Search
CPC ..... A61B 5/318; A61B 5/0006; A61B 5/7275; A61B 5/349; A61B 5/1116; A61B 5/0245; A61B 5/7267; A61B 5/366; A61B 5/4836; A61B 5/316; A61B 5/384; A61B 5/364; A61B 5/377; A61B 5/7221; A61B 5/24; A61B 5/28; A61B 5/36; A61B 5/486;
(Continued)

(56) References Cited

U.S. PATENT DOCUMENTS

2019/0231206 A1 8/2019 Tran et al.
2019/0365267 A1* 12/2019 Aranda Hernandez ......................
A61N 1/36507
2020/0401684 A1 12/2020 Vath et al.

OTHER PUBLICATIONS

Vandenberk, Bert, et al., "Which QT Correction Formulae to Use for QT Monitoring?", J Am Heart Assoc. 2016;5:e003264 doi: 10.1161/JAHA.116.003264, Downloaded from http://ahajournals.org by on Sep. 19, 2022, 15 pgs.

* cited by examiner

*Primary Examiner* — Deborah L Malamud
(74) *Attorney, Agent, or Firm* — Nelson Mullins Riley & Scarborough LLP

(57) ABSTRACT
Systems and methods for ambulatory detection of Q wave-to-T wave (QT) interval prolongation are discussed. A medical-device system comprises a controller circuit and a user interface device. The controller circuit includes a long QT syndrome (LQTS) detector that measures a QT interval from a subcutaneous cardiac signal sensed from a patient using implantable electrodes, and detects an indication of QT prolongation using the measured QT time interval and a programmable threshold received as a user input from the user interface. The control circuit can adjust device operation based on the detected indication of QT prolongation. An output unit can generate a programmable alert of the QT prolongation corresponding to the user input of the programmable threshold.

20 Claims, 8 Drawing Sheets

(51) Int. Cl.
    *A61B 5/287*         (2021.01)
    *A61B 5/36*          (2021.01)

(58) Field of Classification Search
    CPC ......... A61B 5/346; A61B 5/355; A61B 5/308;
             A61B 5/375; A61B 5/00; A61N 1/37247;
                  A61N 1/3702; A61N 1/37258; A61N
                  1/37; A61N 1/0504; A61N 1/08; A61N
                  1/3606; A61N 1/36; A61N 1/362; Y10S
                            128/923; Y10S 128/92
    See application file for complete search history.

500

RECEIVE A SUBCUTANEOUS CARDIAC SIGNAL — 510

MEASURE A Q WAVE-TO-T WAVE (QT) TIME INTERVAL — 520

DETECT AN INDICATION OF QT PROLONGATION USING THE MEASURED QT TIME INTERVAL AND A PROGRAMMABLE THRESHOLD — 530

GENERATE A PROGRAMMABLE ALERT ABOUT THE INDICATION OF QT PROLONGATION — 540

ADJUST DEVICE OPERATION BASED ON THE QT PROLONGATION — 550

AMBULATORY DETECTION OF QT PROLONGATION

CLAIM OF PRIORITY

This application claims the benefit of U.S. Provisional Application No. 63/252,846, filed on Oct. 6, 2021, which is hereby incorporated by reference in its entirety.

TECHNICAL FIELD

This document relates generally to medical devices, and more particularly, to systems, devices, and methods for ambulatory detection of Q wave-to-T wave (QT) interval prolongation.

BACKGROUND

Implantable medical devices (IMDs) have been used for monitoring patient health condition or disease states and delivering therapies. For example, implantable cardioverter-defibrillators (ICDs) may be used to monitor for certain abnormal heart rhythms (also known as arrhythmias) and to deliver electrical energy to the heart to correct the abnormal rhythms. Some IMDs may be used to monitor for chronic worsening of cardiac hemodynamic performance, such as due to congestive heart failure (CHF), and to provide cardiac stimulation therapies to correct cardiac dyssynchrony within a ventricle or between ventricles.

Long QT syndrome (LQTS) is a heart rhythm condition that occurs as the result of a defect in the ion channels of the heart, causing a delay in the time it takes for the heart's electrical system to recharge after each heartbeat. The QT interval is the section on the electrocardiogram (ECG) from the onset point of a Q wave to the end of the T wave in the same cardiac cycle. The Q wave corresponds to the beginning of ventricular depolarization, and the T wave end corresponds to the end of ventricular repolarization. QT interval is generally heart rate-dependent: it is longer when the heart rate is slower and shorter when the heart rate is faster. To make the diagnostic of LQTS independent of heart rate, heart rate-corrected QT interval (QTc) can be computed, such as by using the Bazett formula: QT interval divided by the square root of the R-R interval. Other heart rate-based correction methods have also been used, including linear regression formulae such as Hodges, Fridericia, Framingham, or a nomogram for heart rate-corrected QT.

The normal QT interval varies depending on age and gender, but generally falls with a range. When the QT interval (or the QTc) is longer than normal, LQTS may be diagnosed. LQTS can cause fast, chaotic heartbeats, and increase the risk for Torsade de Pointes, a potentially fatal polymorphic ventricular tachycardia that arises during abnormal ventricular repolarization and may degenerate into ventricular fibrillation. In some patients, LQTS may trigger sudden faint (syncope) with little or no warning sign, or cause seizures. In some severe cases, LQTS can cause sudden death.

LQTS can be congenital or acquired. Congenital LQTS is usually inherited, and associated with abnormality in the gene code for the ion channels. The abnormality of the ion channels slows the recovery phase of the heartbeat. Acquired LQTS is caused by certain medications, mineral imbalances, or medical conditions. Sensitivity to these medications may be related to genetic cause. Inherited LQTS is LQTS common in children and young adults, while acquired LQTS can affect patients of all ages.

LQTS is usually diagnosed in a hospital or a doctor's office by measuring the QT interval on the ECG. Prolongation of the QTc on the 12-lead ECG is a primary marker of Torsade de Pointes risk, and a major drug safety benchmark. Exercise stress test has also been used clinically to diagnose LQTS. However, in some patients, LQTS symptoms are not persistent, and tend to reoccur under certain conditions. In some patients, QT prolongation may not be detected in the doctor's office. Ambulatory monitoring and timely detection and diagnosis of LQTS are clinically important to prevent life-threatening arrhythmias or other adverse events.

OVERVIEW

The present invention discloses, among other things, systems, devices, and methods for ambulatory detection of QT prolongation which predisposes patients to dangerous cardiac arrhythmias, and automatic adjustment of device operations based on the QT prolongation. The LQTS can be diagnosed using subcutaneous cardiac signal (e.g., ECG) sensed by an implantable device coupled to subcutaneously implanted electrodes. According to one embodiment, a medical-device system comprises a controller circuit and a user interface device. The controller circuit includes a long QT syndrome (LQTS) detector that measures a QT interval from a subcutaneous cardiac signal sensed from a patient using implantable electrodes, and detects an indication of QT prolongation using the measured QT time interval and a programmable threshold received as a user input from the user interface. The control circuit can adjust device operation based on the detected indication of QT prolongation. The user interface can include an output unit to generate a programmable alert of the QT prolongation corresponding to the user input of the programmable threshold to a user.

Example 1 is a medical-device system for monitoring a patient, comprising: a controller circuit, including a long QT syndrome (LQTS) detector configured to: receive a subcutaneous cardiac signal sensed from the patient; measure a Q wave-to-T wave (QT) time interval from the subcutaneous cardiac signal; and detect an indication of QT prolongation using the measured QT time interval and a programmable threshold; and a user interface configured to receive a user input of the programmable threshold, the user interface including an output unit configured to generate a programmable alert of the detected indication of QT prolongation corresponding to the user input of the programmable threshold.

In Example 2, the subject matter of Example 1 optionally includes a sensing circuit configured to sense the subcutaneous cardiac signal including a subcutaneous electrocardiogram (S-ECG) via one or more subcutaneously implanted electrodes in the patient.

In Example 3, the subject matter of Example 2 optionally includes the LQTS detector that can be configured to generate a representative S-ECG segment from an ensemble of segments of S-ECG in multiple cardiac cycles, and to measure the QT time interval using the representative S-ECG.

In Example 4, the subject matter of any one or more of Examples 1-3 optionally includes the LQTS detector that can be configured to generate a QT time interval trend under different postures or physical activities of the patient, and to detect the indication of QT prolongation at different postures or physical activities; and the output unit that can be configured to display the QT time interval trend and the indication of QT prolongation at different postures or physical activities.

In Example 5, the subject matter of any one or more of Examples 1-4 optionally includes the LQTS detector that can be configured to generate a QT time interval trend during a course of treatment of the patient, and to detect the indication of QT prolongation during the course of treatment; and the output unit that can be configured to display the QT time interval trend and the indication of QT prolongation during the course of treatment.

In Example 6, the subject matter of any one or more of Examples 1-5 optionally includes the LQTS detector that can be configured to detect the indication of QT prolongation based on a difference between the measured QT time interval and a baseline QT time interval under a baseline condition of the patient.

In Example 7, the subject matter of any one or more of Examples 1-6 optionally includes the LQTS detector that can be configured to measure the QT time interval and to detect the indication of QT prolongation in response to cardiac arrhythmia, or frequent non-sustained arrhythmia episodes exceeding a frequency threshold.

In Example 8, the subject matter of any one or more of Examples 1-7 optionally includes the LQTS detector that can be configured to measure the QT time interval and to detect the indication of QT prolongation at a specific posture state.

In Example 9, the subject matter of any one or more of Examples 1-8 optionally includes the LQTS detector that can be configured to measure the QT time interval and to detect the indication of QT prolongation in response to an initiation of a therapy or a change of therapy.

In Example 10, the subject matter of any one or more of Examples 1-9 optionally includes a memory circuit configured to store at least a portion of the subcutaneous cardiac signal in response to the indication of QT prolongation.

In Example 11, the subject matter of Example 10 optionally includes the controller circuit that can be configured to dynamically adjust a memory space of the memory circuit allocated for storing the subcutaneous cardiac signal based on a type of cardiac event detected from the patient.

In Example 12, the subject matter of any one or more of Examples 1-11 optionally includes the controller circuit that can be configured to adjust a cardiac sensing parameter based on the indication of QT prolongation.

In Example 13, the subject matter of Example 12 optionally includes the controller circuit that can adjust a cardiac sensing parameter including extending a post-ventricular event refractory period by an amount based on the detected indication of QT prolongation.

In Example 14, the subject matter of any one or more of Examples 12-13 optionally includes the controller circuit that can be configured to generate a QT time interval trend over time, and to adjust the cardiac sensing parameter further based on the QT time interval trend.

In Example 15, the subject matter of any one or more of Examples 12-14 optionally include a first ambulatory medical device operatively in communication with a second medical device separated from the first ambulatory medical device, wherein the first ambulatory medical device includes the controller circuit configured to communicate a control signal to the second medical device to adjust a cardiac sensing parameter of the second medical device.

Example 16 is a method for monitoring a patient, comprising: receiving a subcutaneous cardiac signal sensed from the patient; measuring, via a controller circuit, a Q wave-to-T wave (QT) time interval from the subcutaneous cardiac signal; detecting, via the controller circuit, an indication of QT prolongation using the measured QT time interval and a programmable threshold; and generating, via an output unit, a programmable alert of the detected indication of QT prolongation corresponding to the programmable threshold.

In Example 17, the subject matter of Example 16 optionally includes the subcutaneous cardiac signal that can include a subcutaneous electrocardiogram (S-ECG) sensed using one or more subcutaneously implanted electrodes in the patient. The subject matter further includes generating a representative S-ECG segment from an ensemble of segments of S-ECG in multiple cardiac cycles, and measuring the QT time interval using the representative S-ECG.

In Example 18, the subject matter of any one or more of Examples 16-17 optionally includes measuring the QT interval and detecting the QT prolongation triggered by one or more triggering events, including: a cardiac arrhythmia; frequent non-sustained arrhythmia episodes; a specific posture state; or an initiation of a therapy or a change of therapy.

In Example 19, the subject matter of any one or more of Examples 16-18 optionally includes: storing at least a portion of the subcutaneous cardiac signal in response to the indication of QT prolongation; and dynamically adjusting a memory space of a memory device allocated for storing the subcutaneous cardiac signal based on a type of cardiac event detected from the patient.

In Example 20, the subject matter of any one or more of Examples 16-19 optionally includes adjusting a cardiac sensing parameter based on the indication of QT prolongation.

In Example 21, the subject matter of Example 20 optionally includes adjusting a cardiac sensing parameter that can include extending a post-ventricular event refractory period by an amount based on the detected indication of QT prolongation.

In Example 22, the subject matter of any one or more of Examples 16-21 optionally includes the indication of QT prolongation detected by a first ambulatory medical device. The subject matter further includes communicating a control signal from the first ambulatory medical device to a second medical device separated from and communicatively coupled to the first ambulatory medical device, and adjusting a cardiac sensing parameter of the second medical device.

This Overview is an overview of some of the teachings of the present application and not intended to be an exclusive or exhaustive treatment of the present subject matter. Further details about the present subject matter are found in the detailed description and appended claims. Other aspects of the disclosure will be apparent to persons skilled in the art upon reading and understanding the following detailed description and viewing the drawings that form a part thereof, each of which are not to be taken in a limiting sense. The scope of the present disclosure is defined by the appended claims and their legal equivalents.

BRIEF DESCRIPTION OF THE DRAWINGS

Various embodiments are illustrated by way of example in the figures of the accompanying drawings. Such embodiments are demonstrative and not intended to be exhaustive or exclusive embodiments of the present subject matter.

FIC 1.B is an illustration of an example of a system that includes an insertable medical device such as a subcutaneously insertable cardiac monitor (ICM), subcutaneously insertable loop recorder (ILR), or subcutaneously insertable heart failure monitor (SubQ REM).

Figure 1A:
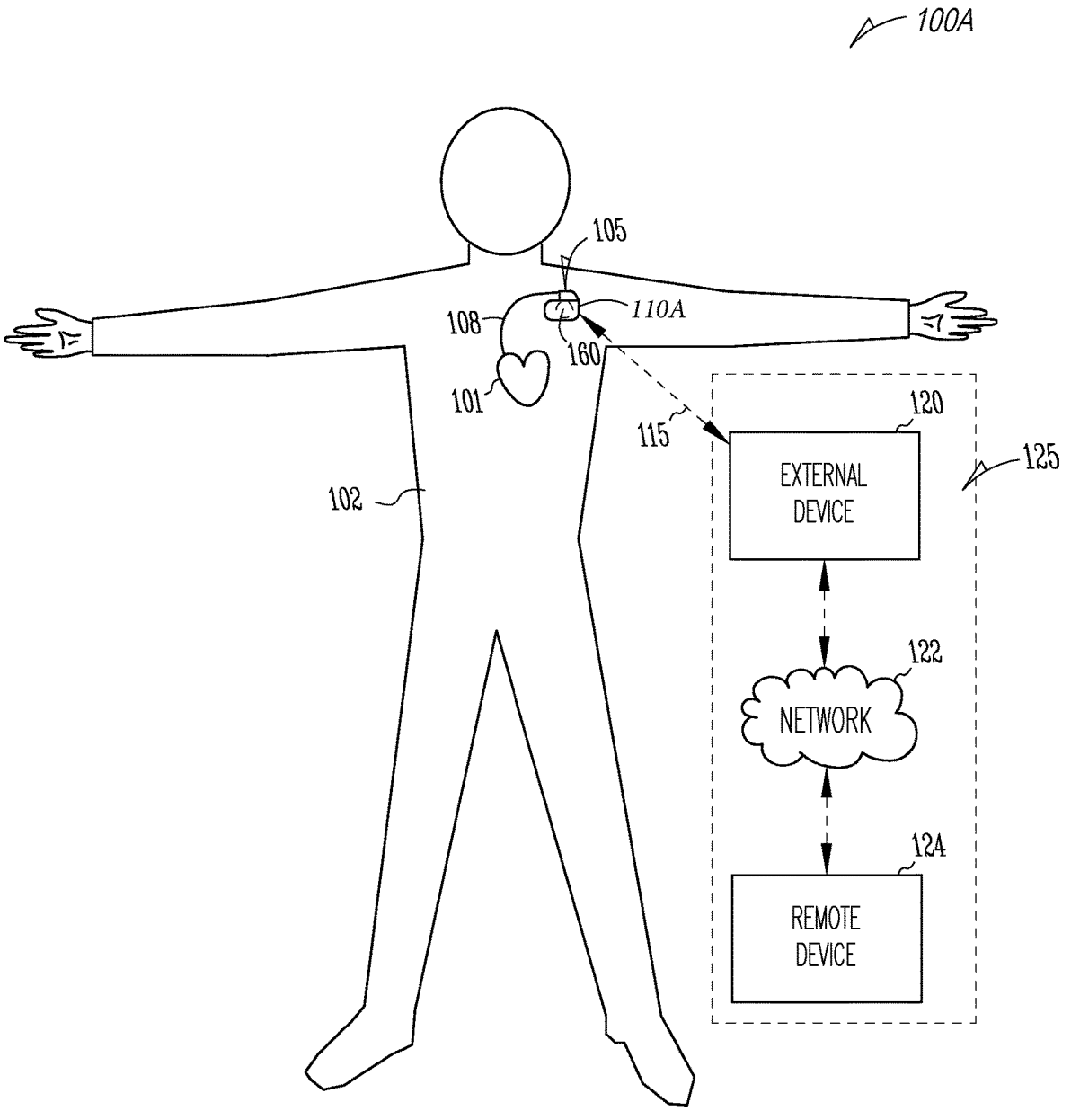
FIG. 1A illustrates generally an example of a patient management system and portions of an environment in which the system may operate.
Figure 1B:
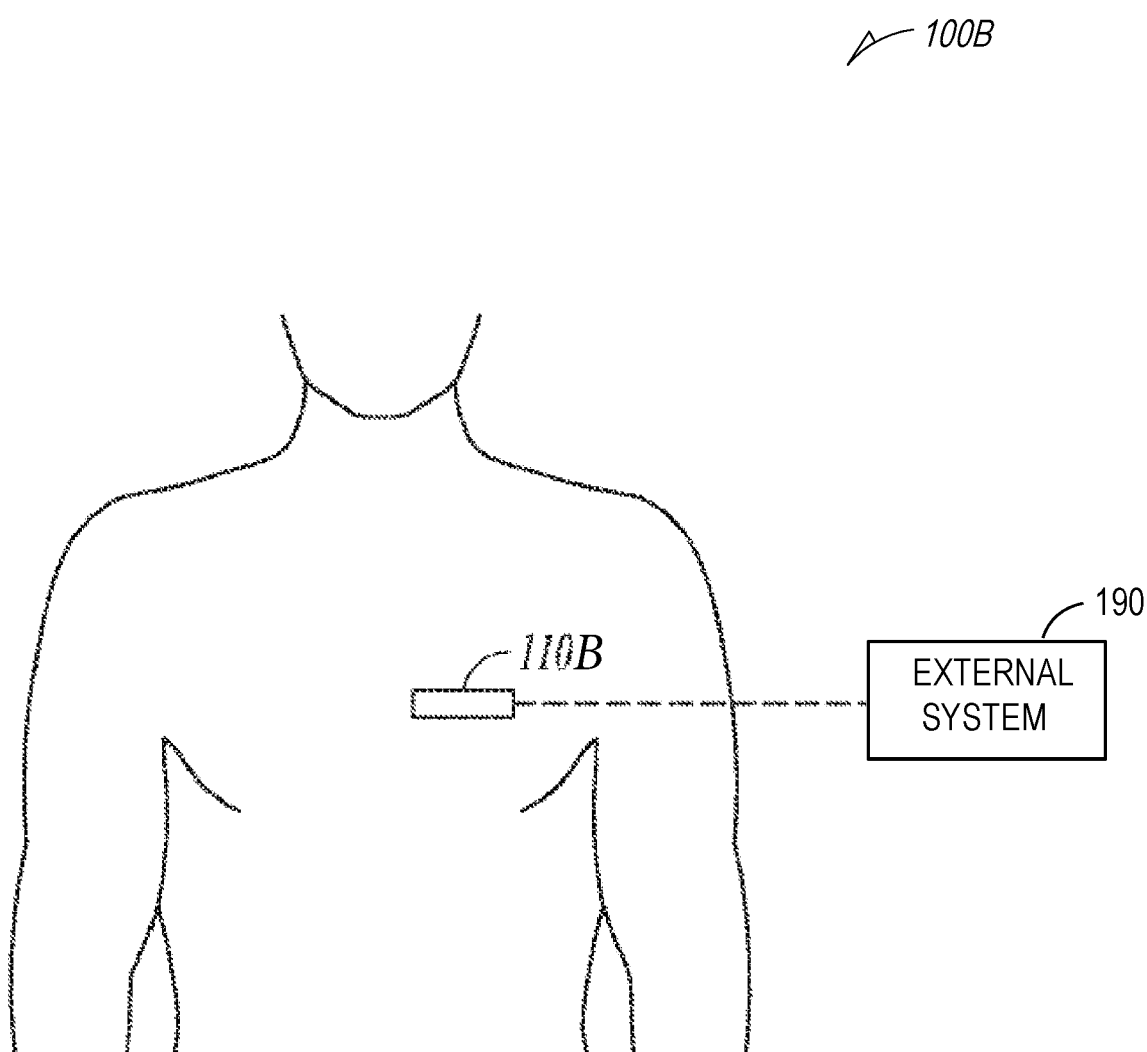
Figure 1C:
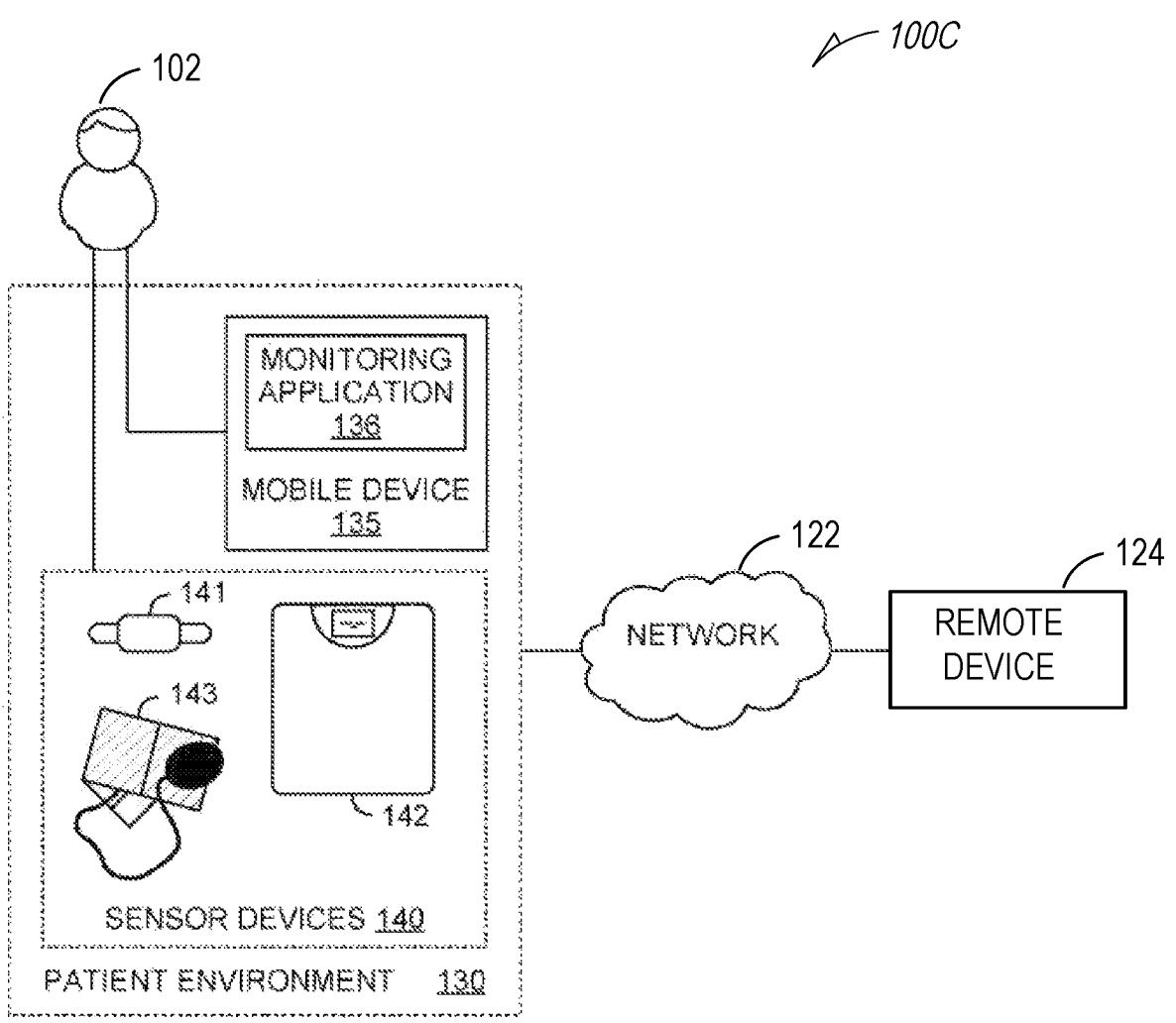

FIG. 1C illustrates an example computing environment that includes wearable or external sensor devices.

Figure 2:
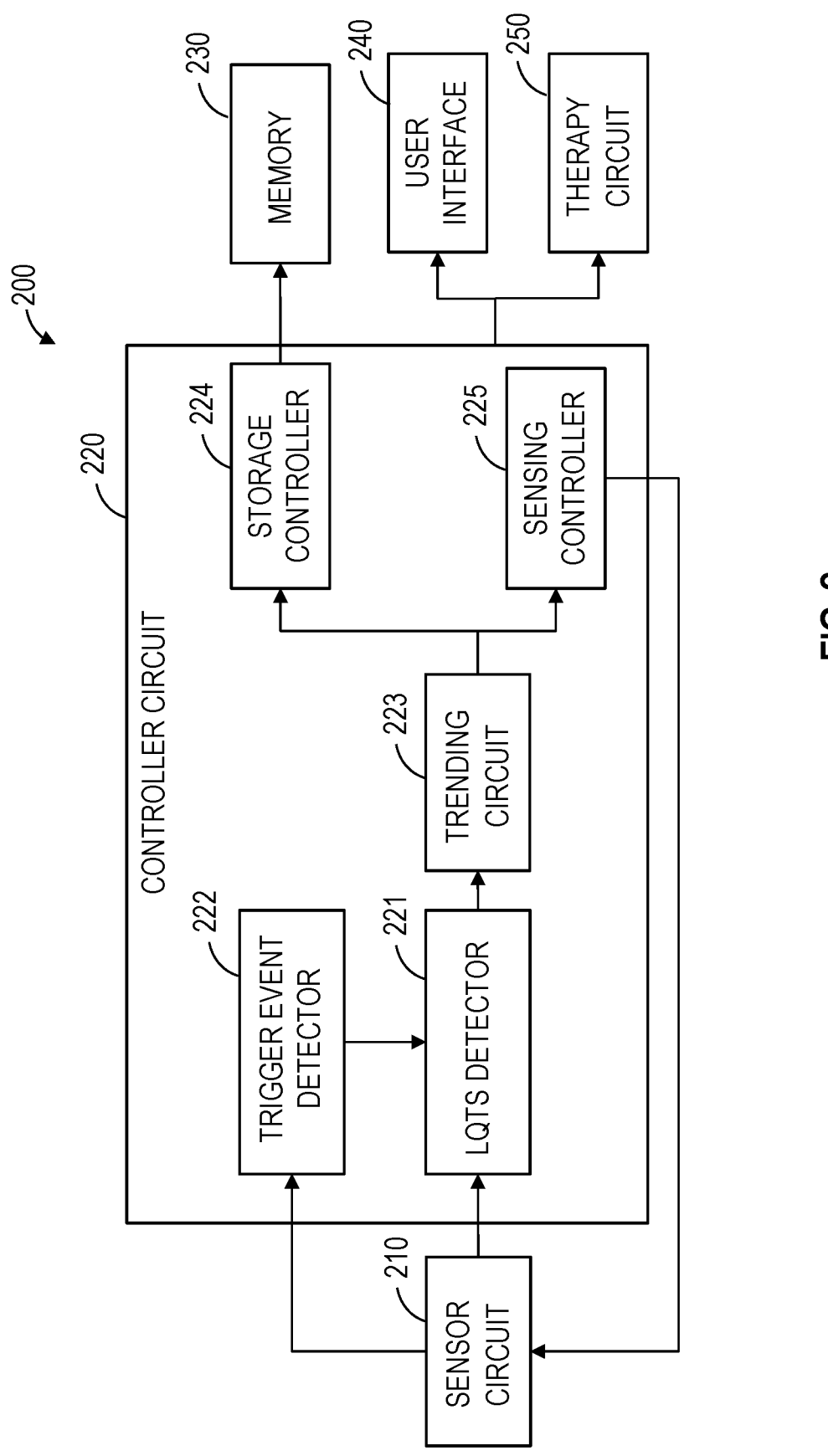

FIG. 2 illustrates generally an example of an arrhythmia detection system configured to detect and indication of QT prolongation.

Figures 3A, 3B:
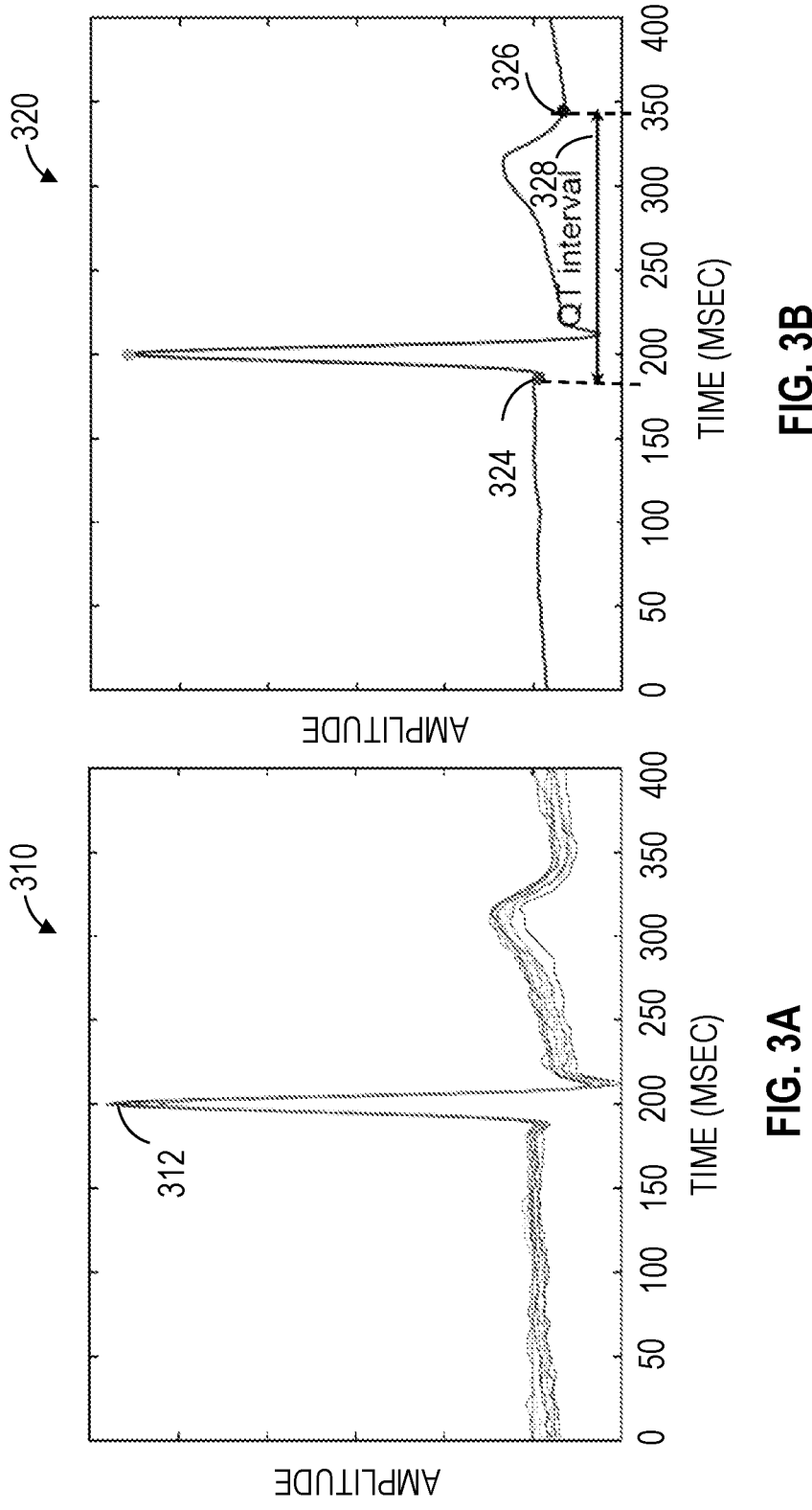

FIGS. 3A-3B illustrate an example of ensemble average of a plurality of S-ECG segments and a QT interval determined from a representative S-ECG segment.

Figures 4A, 4B:
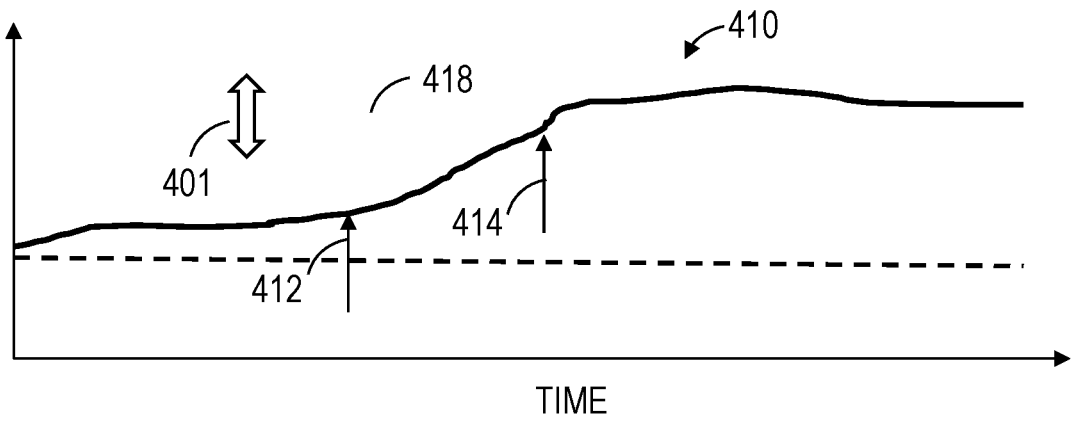

FIG. 4A-4B illustrates examples of a user interface that displays a heart rate-corrected QT (QTc) interval trend along with events occurred during the trending process.

Figure 5:
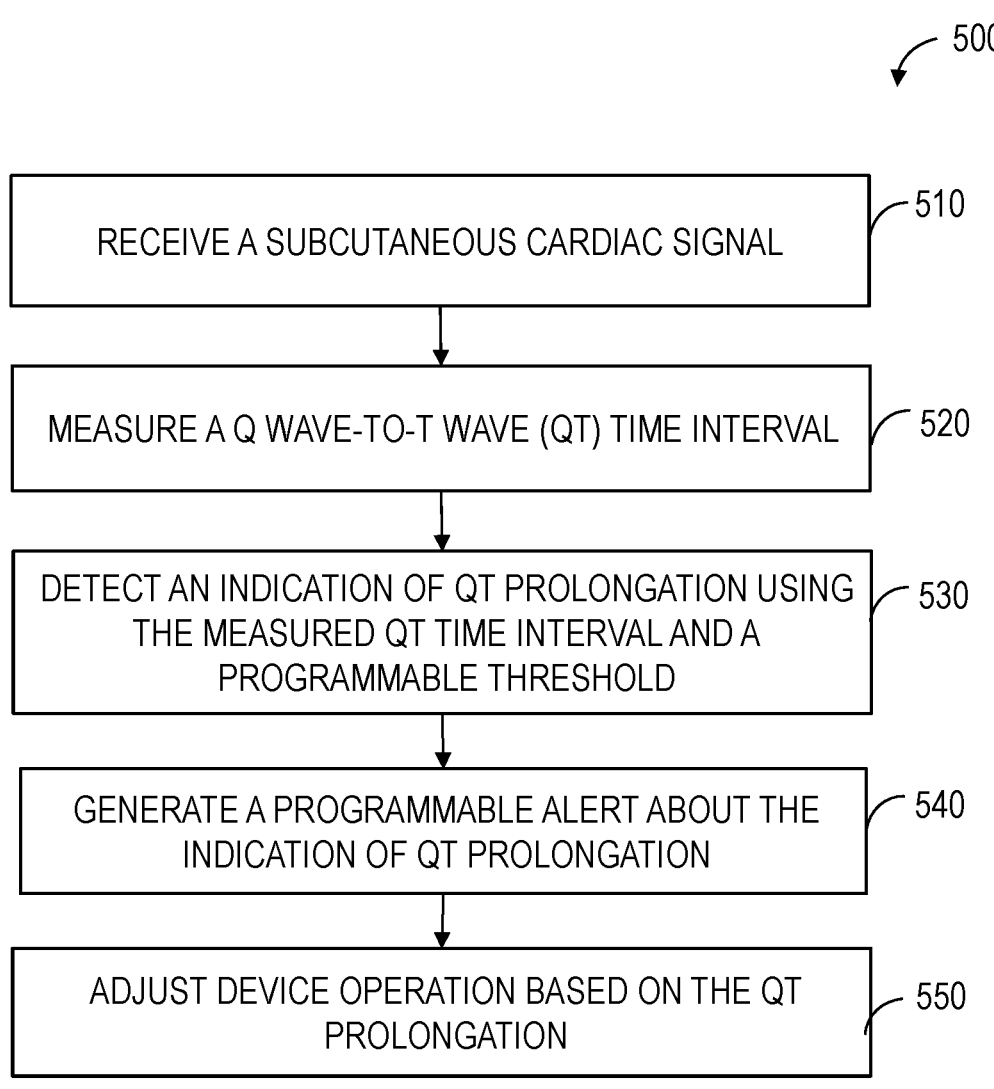

FIG. 5 is a flow diagram illustrating an example of a method for detecting an indication of QT prolongation and adjusting device operation based on the indication of QT prolongation.

Figure 6:
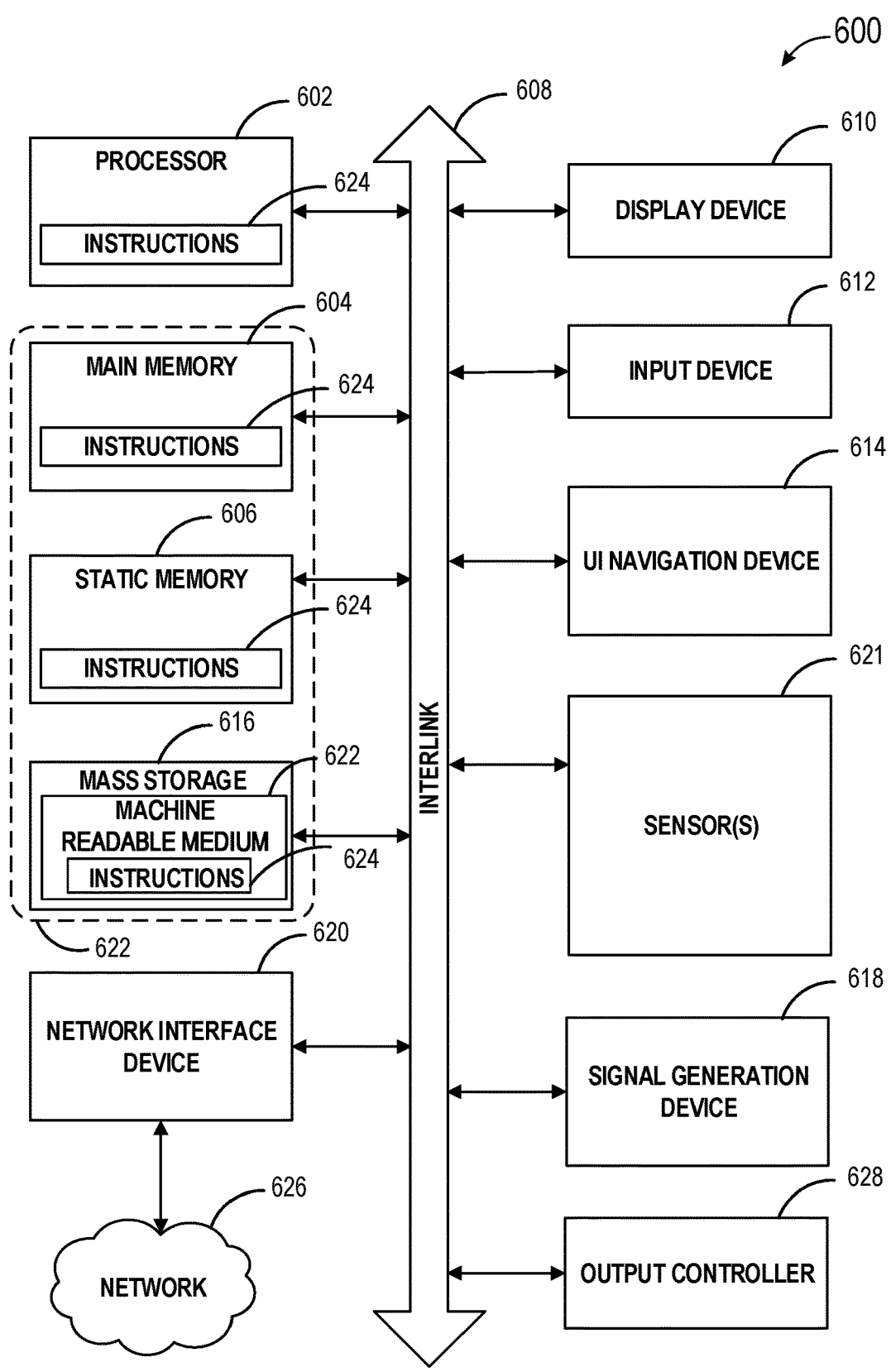

FIG. 6 illustrates generally a block diagram of an example machine upon which any one or more of the techniques (e.g., methodologies) discussed herein may perform.

DETAILED DESCRIPTION

Some IMDs are capable of detecting physiologic events, such as cardiac arrhythmias or progression of chronic heart diseases, and obtaining sampled values of cardiac electrical activity signals such as electrograms. Some IMDs may be communicated with multiple physiologic sensors that may measure various physiological signals. Capturing accurate electrogram or other physiologic sensor information obtained over a longer period of time, such as chronically between regularly-scheduled outpatient office visits, may help the physician re-program the device, if needed, diagnose cardiac disease, or assess the patient's health status.

Long QT syndrome (LQTS) is a form of cardiac arrhythmia that can predispose a person to dangerous cardiac arrhythmias that may lead to unexpected loss of consciousness (syncope), sudden death, and cardiac arrest. Currently, LQTS is typically diagnosed in a controlled clinical setting (e.g., 12-lead ECG in a hospital or a doctor's office) within a short period of time (usually less than 6-12 hours). However, in some patients the LQTS symptoms may be concealed during the office visit (e.g., when the patient is at rest), such that no LQTS can be diagnosed based on the short-time examination in a controlled setting. On the other hand, in such patients LQTS may be provoked in an ambulatory, out-of-hospital setting such as when patients engage in physical activities, or take or adjust medications at home. Ambulatory and long-term patient monitoring can help identify patients with LQTS.

Diagnosis of LQTS is dependent on accurate measurement of QT interval, which may be affected by a number of factors. A wide QRS complex on an ECG may give the appearance that the QT interval is prolonged. However, a wide QRS complex represents depolarization, and LQTS is a disorder of repolarization. Sometimes the end of a T wave may not be clearly defined, which can negatively affect the accuracy of QT measurement. Irregular rhythms can make it difficult to obtain a consistent QT interval measurement. For example, atrial fibrillation can make it difficult to reliably detect a T wave, thus affecting the accuracy of QT interval measurement. QT intervals based on the 12-lead ECG, particularly when measured in relatively short period of time, may be subject to intra-observer and inter-observer variation, resulting from variations in T-wave morphology, noisy baseline, or the presence of U waves. This may cloud the LQTS interpretation and diagnosis.

The present inventors have recognized an unmet need for devices and techniques for automatic and ambulatory detection of QT prolongation in an out-of-hospital setting with improved accuracy and reliability. Disclosed herein are systems, devices, and methods for monitoring a patient and detecting QT prolongation. In accordance with an embodiment, a medical-device system receives a subcutaneous cardiac signal sensed from the patient, such as a subcutaneous ECG (S-ECG) sensed using one or more subcutaneously implanted electrodes. A long QT syndrome (LQTS) detector, which can be included in an implantable device, measures a QT interval from the subcutaneous cardiac signal, and detect therefrom an indication of QT prolongation using a programmable threshold. The measurement of QT interval may be triggered by a specific triggering event. The medical-device system may provide an alert to the user about the detection of QT prolongation, adjust device operation such as data storage and/or data presentation in response to the detection of QT prolongation.

The systems, devices, and methods discussed in this document may improve the medical technology of device-based, ambulatory detection of QT prolongation and diagnosis of LQTS. Compared to 12-lead ECG, the ambulatory S-ECG using the subcutaneously implanted electrodes allows for more flexible (e.g., continuous if desired) patient monitoring over an extended period of time in an ambulatory setting, thereby increasing the chance of capturing QT prolongation in certain patients whose LQTS symptoms are concealed and can be triggered by events such as physical activities, medications, or other treatment received. With improved QT interval measurement, LQTS can be diagnosed more accurately, therapies or other interventions may be timely provided to the patient to prevent fatal arrhythmias or other adverse events, and patient outcome can be improved. Additionally, accurate assessment of QT prolongation can also help reduce false alarms of LQTS diagnosis. Consequently, fewer unnecessary drugs and procedures may be scheduled, prescribed, or provided, and an overall system cost and power savings may be realized in contrast to existing medical devices and systems.

The systems, devices, and methods discussed in this document may improve functionality of a medica device system. According to some examples, the detection of QT prolongation may be used to adjust device operation, such as physiological data storage in a device memory. In accordance with various examples discussed in this document, an ambulatory (e.g., implantable) device can dynamically increase the size of memory space to store more physiological data in response to the detection of QT prolongation. With more stored data, a clinician may review the stored data and adjudicate or confirm LQTS with improved accuracy. In accordance with other examples, in response to the detection of QT prolongation, the ambulatory device can adjust a cardiac sensing parameter to avoid or reduce oversensing of cardiac events. As such, device functionalities with respect to cardiac sensing and event detection (e.g., arrhythmias) may be improved.

FIG. 1A illustrate generally examples of a patient management system 100A and portions of an environment in which the system 100A may operate. The patient management system 100A may perform a range of activities, including remote patient monitoring and diagnosis of a disease condition. Such activities may be performed proximal to a patient, such as in the patient's home or office, through a centralized server, such as in a hospital, clinic or physician's office, or through a remote workstation, such as a secure wireless mobile computing device.

The patient management system 100A may include an ambulatory system 105 associated with a patient 102, an external system 125, and a telemetry link 115 providing for communication between the ambulatory system 105 and the external system 125.

The ambulatory system 105 may include an ambulatory medical device (AMD) 110A. In an example, the AMD 110A may be an implantable device subcutaneously implanted in a chest, abdomen, or other parts of the patient 102. Examples of the implantable device may include, but are not limited to, pacemakers, pacemaker/defibrillators, cardiac resynchronization therapy (CRT) devices, cardiac remodeling control therapy (RCT) devices, neuromodulators, drug delivery devices, biological therapy devices, diagnostic devices such as cardiac monitors or loop recorders, or patient monitors, among others. The AMD 110A alternatively or additionally may be a subcutaneous medical device such as a subcutaneous monitor or diagnostic device, external monitoring or therapeutic medical devices such as automatic external defibrillators (AEDs) or Holter monitors, or wearable medical devices such as patch-based devices, smart watches, or smart accessories.

By way of example, the AMD 110A may be coupled to a lead system 108. The lead system 108 may include one or more transvenously, subcutaneously, or non-invasively placed leads or catheters. Each lead or catheter may include one or more electrodes. The arrangements and uses of the lead system 108 and the associated electrodes may be determined using the patient need and the capability of the AMD 110. The associated electrodes on the lead system 108 may be positioned at the patient's thorax or abdomen to sense a physiological signal indicative of cardiac activity, or physiologic responses to diagnostic or therapeutic stimulations to a target tissue. By way of example and not limitation, and as illustrated in FIG. 1, the lead system 108 may be surgically inserted into, or positioned on the surface of, a heart 101. The electrodes on the lead system 108 may be positioned on a portion of a heart 101, such as a right atrium (RA), a right ventricle (RV), a left atrium (LA), or a left ventricle (LV), or any tissue between or near the heart portions. In some examples, the lead system 108 and the associated electrodes may alternatively be positioned on other parts of the body to sense a physiological signal containing information about patient heart rate or pulse rate. In an example, the lead system 108 may include one or more subcutaneous electrodes implanted under the skin configured to sense a subcutaneous electrocardiogram (S-ECG). In an example, the ambulatory system 105 may include one or more leadless sensors not being tethered to the AMD 110A via the lead system 108. The leadless ambulatory sensors may be configured to sense a physiological signal and wirelessly communicate with the AMD 110.

The AMD 110A may be configured as a monitoring and diagnostic device. The AMD 110A may include a hermetically sealed can that houses one or more of a sensing circuit, a control circuit, a communication circuit, and a battery, among other components. The sensing circuit may sense a physiological signal, such as using a physiologic sensor or the electrodes associated with the lead system 108. Examples of the physiological signal may include one or more of electrocardiogram (ECG), intracardiac electrogram, arrhythmia, heart rate, heart rate variability, intrathoracic impedance, intracardiac impedance, arterial pressure, pulmonary artery pressure, left atrial pressure, right ventricular (RV) pressure, left ventricular (LV) coronary pressure, coronary blood temperature, blood oxygen saturation, one or more heart sounds, intracardiac acceleration, physical activity or exertion level, physiologic response to activity, posture, respiration rate, tidal volume, respiratory sounds, body weight, or body temperature.

The AMD 110A may include a physiologic event detector circuit 160 configured to detect a physiologic event using the sensed physiological signal. An example of the physiologic event being detected is a long QT syndrome (LQTS). The physiologic event detector circuit 160 can measure QT interval, correct the QT time interval for patient instantaneous heart rate, and determine an indication of QT prolongation using the measured QT time interval and a programmable threshold. In some examples, the physiologic event detected by the physiologic event detector circuit 160 can include a cardiac arrhythmic event, such as atrial fibrillation (AF), atrial flutter, atrial tachycardia, supraventricular tachycardia, ventricular tachycardia, or ventricular fibrillation, cardiac pauses, among other brady- or tachy-arrhythmia. In some examples, the physiologic event detector circuit 160 may operate in a patient-triggered mode, register a patient-triggered event, and record physiologic data in response to a user-activated trigger. The trigger may be activated by the patient when the patient demonstrates signs or symptoms, or experiences a precursor event indicative of a medical event.

In some examples, the physiologic event detector circuit 160 may extract from the sensed physiological signal a signal characteristic, and determine a confidence indicator for the detected physiologic event using the signal characteristic. The confidence indicator indicates a likelihood that the detected physiologic event is present. The confidence indicator may have a categorical or numerical value. Alternatively, in some examples, the confidence indicator for the physiologic event detected by AMD 110A may be evaluated by an external device, such as one in the external system 125.

The AMD 110A may alternatively be configured as a therapeutic device configured to treat arrhythmia or other heart conditions. The AMD 110A may include a therapy unit that may generate and deliver one or more therapies. The therapy may be delivered to the patient 102 via the lead system 108 and the associated electrodes. The therapies may include electrical, magnetic, or other types of therapy. The therapy may include anti-arrhythmic therapy to treat an arrhythmia or to treat or control one or more complications from arrhythmia, such as syncope, congestive heart failure, or stroke, among others. Examples of the anti-arrhythmic therapy may include pacing, cardioversion, defibrillation, neuromodulation, drug therapies, or biological therapies, among other types of therapies. In an example, the therapies may include cardiac resynchronization therapy (CRT) for rectifying dyssynchrony and improving cardiac function in CHF patients. In some examples, the AMD 110A may include a drug delivery system such as a drug infusion pump to deliver drugs to the patient for managing arrhythmia or complications from arrhythmia.

The external system 125 may include a dedicated hardware/software system such as a programmer, a remote server-based patient management system, or alternatively a system defined predominantly by software running on a standard personal computer or a mobile device. The external system 125 may manage the patient 102 through the AMD 110A connected to the external system 125 via a communication link 115. This may include, for example, programming the AMD 110A to perform one or more of acquiring physiologic data, performing at least one self-diagnostic test (such as for a device operational status), analyzing the physiologic data to detect a cardiac arrhythmia, or optionally delivering or adjusting a therapy to the patient 102. Additionally, the external system 125 may receive device data from the AMD 110A via the communication link 115. Examples of the device data received by the external system 125 may include real-time or stored physiologic data from the patient 102, diagnostic data such as detection of cardiac arrhythmia or events of worsening heart failure, responses to therapies delivered to the patient 102, or device operational status of the AMD 110A (e.g., battery status and lead impedance). The telemetry link 115 may be an inductive telemetry link, a capacitive telemetry link, or a radio-frequency (RF) telemetry link, or wireless telemetry based on, for example, "strong" Bluetooth or IEEE 802.11 wireless fidelity "WiFi" interfacing standards. Other configurations and combinations of patient data source interfacing are possible.

By way of example and not limitation, the external system 125 may include an external device 120 in proximity of the AMD 110A, and a remote device 124 in a location relatively distant from the AMD 110A in communication with the external device 120 via a telecommunication network 122. Examples of the external device 120 may include a programmer device.

The remote device 124 may be configured to evaluate collected patient data and provide alert notifications, among other possible functions. In an example, the remote device 124 may include a centralized server acting as a central hub for collected patient data storage and analysis. The server may be configured as a uni-, multi- or distributed computing and processing system. The remote device 124 may receive patient data from multiple patients including, for example, the patient 102. The patient data, such as medical event events, may be collected by the AMD 110A, among other data acquisition sensors or devices associated with the patient 102. The remote device 124 may include a storage unit to store the patient data in a patient database. The remote device 124 may include an alert analyzer circuit to evaluate the collected patient data to determine if specific alert condition is satisfied. Satisfaction of the alert condition may trigger a generation of alert notifications. In some examples, the alert conditions may alternatively or additionally be evaluated by the AMD 110. In an example of monitoring patient QT intervals, the alert can be a QT prolongation alert in response to an indication of QT prolongation as detected by the physiologic event detector circuit 160. By way of example, alert notifications may include a Web page update, phone or pager call, E-mail, SMS, text, or "Instant" message, as well as a message to the patient and a simultaneous direct notification to emergency services and to the clinician. Other alert notifications are possible.

In some examples, the external device 120 or the remote device 124 may include a medical event prioritizer circuit configured to prioritize the alert notifications. Prioritization of the alert notifications may be based on a confidence indicator of the physiologic event being detected. The confidence indicator may be generated by the AMD 110A, or alternatively by the external device 120 or the remote device 124. In the event that multiple arrhythmic events are detected with respective confidence indicators, the alert notifications and the physiological signals associated with the arrhythmic events may be prioritized in a specific order (e.g., a descending order, or an ascending order) of confidence indicators. The arrhythmic events may be presented to a user for event review or adjudication, or to a process for arrhythmia confirmation, in accordance with the prioritized order.

The remote device 124 may additionally include one or more locally configured clients or remote clients securely connected over the network 122 to the server. Examples of the clients may include personal desktops, notebook computers, mobile devices, or other computing devices. Users, such as clinicians or other qualified medical specialists, may use the clients to securely access stored patient data assembled in the database in the server, and to select and prioritize patients and alerts for health care provisioning. The remote device 124, including the server and the interconnected clients, may execute a follow-up scheme by sending follow-up requests to the AMD 110A, or by sending a message or other communication to the patient 102, clinician or authorized third party as a compliance notification.

The network 122 may provide wired or wireless interconnectivity. In an example, the network 122 may be based on the Transmission Control Protocol/Internet Protocol (TCP/IP) network communication specification, although other types or combinations of networking implementations are possible. Similarly, other network topologies and arrangements are possible, which may include, for example, user datagram protocol (UDP), hypertext transfer protocol (HTTP), a local area network (LAN), a wide area network (WAN), a packet data network (e.g., the Internet), mobile telephone networks (e.g., cellular networks), Plain Old Telephone (POTS) networks, and wireless data networks, among others.

One or more of the external device 120 or the remote device 124 may output the detected medical events to a user such as the patient or a clinician, or to a process including, for example, an instance of a computer program executable in a microprocessor. In an example, the process may include an automated generation of recommendations for a therapy, or a recommendation for further diagnostic test or treatment. In an example, the external device 120 or the remote device 124 may respectively include display units for displaying the physiological signals, or alerts, alarms, emergency calls, or other forms of warnings to signal the detection of arrhythmia. In some examples, the external system 125 may include an external data processor configured to analyze the physiologic or functional signals received by the AMD 110A, and to confirm or reject the detection of the medical events. Computationally intensive algorithms, such as machine-learning algorithms, may be implemented in the external data processor to process the data retrospectively to detect cardiac arrhythmia.

Portions of the AMD 110A or the external system 125 may be implemented using hardware, software, firmware, or combinations thereof. Portions of the AMD 110A or the external system 125 may be implemented using an application-specific circuit that may be constructed or configured to perform one or more particular functions, or may be implemented using a general-purpose circuit that may be programmed or otherwise configured to perform one or more functions. Such a general-purpose circuit may include a microprocessor or a portion thereof, a microcontroller or a portion thereof, or a programmable logic circuit, a memory circuit, a network interface, and various components for interconnecting these components. For example, a "comparator" may include, among other things, an electronic circuit comparator that may be constructed to perform the specific function of a comparison between two signals or the comparator may be implemented as a portion of a general-purpose circuit that may be driven by a code instructing a portion of the general-purpose circuit to perform a comparison between the two signals.

FIG. 1B is an illustration of an example of a system 100B that includes an insertable medical device 110B (e.g., a subcutaneously insertable cardiac monitor (ICM), subcutaneously insertable loop recorder (ILR), or subcutaneously insertable heart failure monitor (SubQ HFM)) and an external system 190. The insertable medical device 110B may be a diagnostic-only device that senses electrical signals of the heart and, depending on the device, other signals of the heart or other physiologic signals. Similar to the external system 125 as shown in FIG. 1A, the external system 190 may include a programmer that communicates one or more wireless signals with the insertable medical device 110B, such as by using radio frequency (RF) or by one or more other telemetry methods. The external system 190 can communicate information with the insertable medical device 110B to configure operation of the insertable medical device 110B by downloading, operating parameters to the insertable device, and to upload data recorded by the insertable device without removal of the device.

The insertable medical device 110B includes a housing that may include a conductive material (e.g,. titanium) or may include a non-conductive, non-metallic, non-magnetic material, such as a glass, porcelain, a non-conductive polymer, etc. The insertable medical device 110B may include two or more electrodes on the housing of the device to sense the electrical signals of the heart or other physiologic sensors of the patient or subject. In certain examples, the electrodes are arranged on a subcutaneously implantable or insertable lead in contact with subcutaneous tissues and/or muscle. in some examples, the electrodes are arranged on the device itself.

Subcutaneously insertable devices such as ICMs, ILRs, and SubQ HFMs are useful to monitor specific aspects of the physiology of a patient for extended periods of time while the patient is away from a clinical setting. For example, an ICM may be used to detect episodes of atrial fibrillation (AF) of the patient. The episodes can be totaled or trended to determine an AF burden of the patient. In another example, the subcutaneously insertable devices can be used to monitor progression of heart failure of the patient while the patient is away from a clinical setting.

FIG. 1C illustrates an example computing environment 100C that includes wearable or external sensor devices. As shown, the computing environment 100A may include a patient environment 130 connected to a remote device 124 via a network 122 (as the remote device and the network as shown in FIG. 1A). The remote device 124 and the patient environment 130 allow a care provider (e.g., a technician, nurse, physician, etc.) to monitor physiological data generated by the patient 102.

The patient environment 130 includes a mobile device 135 and the at least one sensor device 140. The mobile device 135 includes the monitoring application 136 which permits communication between the at least one sensor device 140 and the remote device 124 via the network 122. The monitoring application 136 may configure the at least one sensor device 140 (e.g., IoT devices) to monitor physiological data of the one or more patient 102 as specified by a care plan. For example, the monitoring application 136 could configure logic on a heart rate monitoring device worn by the patient to monitor the patient's heart rate. in turn, the monitoring application 135 can send the heart rate data to the remote device 124 which determines if a heath event is triggered, and if so, executes a workflow to process the event as described above. in another example, the heart rate monitoring device, upon detecting that a threshold condition has been satisfied, could generate and transmit a health event to the mobile device 135, which in turn transmits the health event to the remote device 124 for processing. However, in other examples, some of the tasks performed by the remote device 124 may be performed by the mobile device 135. That is, the workflow may include tasks performed by the mobile device 135 or the at least one sensor device 140 as well as tasks performed by the remote device 124.

In one example, the monitoring application 136 may use an output device (e.g., a display or audio system) on the mobile device 135 to provide information to the patient 102. For example, when executing a workflow, the patient 102 may be asked if he or she is experiencing any symptoms. To obtain feedback from the patient 102, the monitoring application 1.36 may display a user interface (UI) on the mobile device 135 which permits the patient 102 to list symptoms. Moreover, the monitoring application 136 may also display general information related to a care plan or the at least one sensor device 140 such as the patient's heart rate or weight, status of the at least one sensor device 140, etc.

In one example, the at least one sensor device 140 interacts with the monitoring application 136 and assists the patient 102 in reporting patient vitals and other information to the remote device 124. As shown, the at least one sensor device 140 may include a body sensor 141, a weighing scale 142. and a blood pressure cuff 143. Each of the at least one sensor device 140 may capture different vitals of the patient 102. For example, when applied to a body of patient 102, the body sensor 141 captures physiological data (e.g., heart rate, ECG data, etc.) in real-time. In addition, each of the at least one sensor device 140 may be configured to transmit body-related metrics electronically to the monitoring application 136 on the mobile device 135. In turn, the monitoring application 136 sends the captured metrics to the remote device for further analysis.

FIG. 2 illustrates generally an example of an arrhythmia detection system 200 configured to detect, among other things, QT prolongation. Portions of the system 200 may be included in the physiologic event detector circuit 160 of the AMD 110A, the insertable medical device 110B, or the external system 125.

The system 200 may include one or more of a sensor circuit 210, a controller circuit 220, a memory 230, and a user interface unit 240. The system 200 may additionally include an optional therapy circuit 250. The sensor circuit 210 may include circuitry configured to sense a physiological signal in a patient via one or more implantable, wearable, or otherwise ambulatory sensors or electrodes associated with the patient. The sensors or electrodes may be included in, or otherwise associated with an ambulatory device such as the AMD 110A or the insertable medical device 110B via a wired or a wireless communication link. In some examples, the sensors or electrodes may be incorporated into an implantable cardiac monitor (ICM) device configured for subcutaneous implantation. In some examples, the sensors or electrodes may be incorporated into an external monitor such as a wearable ECG recorder or wearable medical devices such as a patch-based device, smart watch, or smart accessory. Examples of the physiological signals may include surface electrocardiography (ECG) sensed from electrodes placed on the body surface, subcutaneous ECG (S-ECG) sensed from electrodes placed under the skin, intracardiac electrogram (EGM) sensed from the one or more electrodes on the lead system 108, thoracic or cardiac impedance signal, arterial pressure signal, pulmonary artery pressure signal, left atrial pressure signal, RV pressure signal, LV coronary pressure signal, coronary blood temperature signal, blood oxygen saturation signal, heart sound signal such as sensed by an ambulatory accelerometer or acoustic sensors, physiologic response to activity, apnea hypopnea index, respiration signals such as a respiration rate signal or a tidal volume signal, brain natriuretic peptide (BNP), blood panel, sodium and potassium levels, glucose level and other biomarkers and bio-chemical markers, among others. The sensor circuit 210 may include one or more sub-circuits to digitize, filter, or perform other signal conditioning operations on the received physiological signal.

The controller circuit 220, coupled to the sensor circuit 210, may detect an indication of QT prolongation from a subcutaneous cardiac signal, and adjust device operation based on the detected indication of QT prolongation. The controller circuit 220 may be implemented as a part of a microprocessor circuit, which may be a dedicated processor such as a digital signal processor, application specific integrated circuit (ASIC), microprocessor, or other type of processor for processing information including physical activity information. Alternatively, the microprocessor circuit may be a general-purpose processor that may receive and execute a set of instructions of performing the functions, methods, or techniques described herein.

The controller circuit 220 may include circuit sets comprising one or more other circuits or sub-circuits, including a LQTS detector 221, a trigger event detector 222, a trending circuit 223, a storage control 224, and a sensing controller 225. These circuits may, alone or in combination, perform the functions, methods, or techniques described herein. In an example, hardware of the circuit set may be immutably designed to carry out a specific operation (e.g., hardwired). In an example, the hardware of the circuit set may include variably connected physical components (e.g., execution units, transistors, simple circuits, etc.) including a computer readable medium physically modified (e.g., magnetically, electrically, moveable placement of invariant massed particles, etc.) to encode instructions of the specific operation. In connecting the physical components, the underlying electrical properties of a hardware constituent are changed, for example, from an insulator to a conductor or vice versa. The instructions enable embedded hardware (e.g., the execution units or a loading mechanism) to create members of the circuit set in hardware via the variable connections to carry out portions of the specific operation when in operation. Accordingly, the computer readable medium is communicatively coupled to the other components of the circuit set member when the device is operating. In an example, any of the physical components may be used in more than one member of more than one circuit set. For example, under operation, execution units may be used in a first circuit of a first circuit set at one point in time and reused by a second circuit in the first circuit set, or by a third circuit in a second circuit set at a different time.

The LQTS detector 221 can measure a QT interval from a cardiac signal, such as a subcutaneous electrocardiogram (S-ECG) signal sensed from the patient by the sensor circuit 210. The QT interval represents a time interval from the onset point of a Q wave of a cardiac cycle to the end of the T wave in the same cardiac cycle. To improve the accuracy of detecting and Q wave and T wave, in an example, the LQTS detector 221 can generate a representative S-ECG segment from an ensemble of a plurality of segments of S-ECG during respective cardiac cycles, detect Q wave and T wave from the representative S-ECG segment, and measure the QT interval from the onset point of Q wave to the end of T wave. In an example, the representative S-ECG segment can be determined as an ensemble average of the plurality of S-ECG segments over multiple cardiac cycles. An example of averaging the S-ECG segments and measuring the QT interval from the ensemble-averaged S-ECG segment is illustrated in FIGS. 3A-3B.

As an alternative to determining the QT interval using the representative S-ECG segment (e.g., an ensemble-averaged S-ECG segment 320 as illustrated in FIG. 3B), in some examples, the LQTS detector 221 can detect Q wave and T wave and measure QT interval from each of a plurality of S-ECG segments separately. The LQTS detector 221 can determine a representative QT interval using an average (or another central tendency measure) of the QT intervals respectively measured from the plurality of S-ECG segments.

The LQTS detector 221 can detect an indication of QT prolongation using the measured QT interval and a programmable threshold. A user (e.g., a clinician) can program the threshold value based on age, gender, health status, or medical conditions of the patient. A programmable QT threshold may also allow the user to control alerts or notification of a suspected LQTS diagnosis. In an example, the LQTS detector 221 can correct the measured QT interval for patient heart rates. The heart rate-corrected QT interval (QTc) can be computed using one of known formulae, such as Bazett formula (normalizing the QT interval by the square root of the R-R interval), or a linear regression formula such as Hodges, Fridericia, Framingham, or a QT nomogram. The LQTS detector 221 can detect QT prolongation if QTc interval exceeds a programmable threshold. In an example, the threshold value for the QTc interval can be programmed to approximately 500 milliseconds (msec). An indication of QT prolongation can be generated if QTc interval is greater than 500 msec.

In some examples, the LQTS detector 221 can detect an indication of QT prolongation based on a change of the measured QT or QTc interval from a baseline QT or QTc interval. This may be used to address elevated long QT risk such as due to change of patient health status or medical history (e.g., development of a cardiac disease, initiation or a change of mediation or a therapy). The baseline QT or QTc interval can be determined before the known change of patient health status. If the measured QT or QTc interval exceeds the baseline QT or QTc interval by a programmable margin threshold, then a QT prolongation is indicated. In an example, the margin threshold can be programmed to approximately 60 msec.

The LQTS detector 221 can monitor patient cardiac signal (e.g., S-ECG), measure QT interval, and assess QT prolongation continuously or intermittently at programmable discrete times or time intervals. Alternatively, in some examples, the QT interval measurement and QT prolongation assessment can be initiated in response to a triggering event received or otherwise detected by the trigger event detector 222. In an example, the triggering event is an onset of a specific type of cardiac arrhythmia. The trigger event detector 222 may detect such cardiac arrhythmia, such as an atrial fibrillation, a supraventricular tachyarrhythmia, or a ventricular tachyarrhythmia using physiological signals sensed from the patient such as by the sensor circuit 210. The detected cardiac arrhythmia may trigger the LQTS detector 221 to measure QT intervals and to assess QT prolongation. In an example, the trigger event detector 222 may detect non-sustained arrhythmia episodes during a specific time periods. An arrhythmia episode is non-sustained if it continues for a period shorter than a specific duration and then terminates. Frequent non-sustained arrhythmia episodes may be indicative of LQTS and predicative of more severe cardiac arrhythmia. The trigger event detector 222 may determine a frequency of non-sustained arrhythmias. When the frequency of non-sustained arrhythmia episodes exceeds a frequency threshold, the LQTS detector 221 may be triggered to measure QT intervals and to assess QT prolongation. The non-sustained arrhythmia frequency threshold can be programmable, and based on the type of non-sustained arrhythmia. In an example, for non-sustained ventricular tachyarrhythmia, the non-sustained arrhythmia frequency threshold can be one episode per day. In an example, for non-sustained atrial tachyarrhythmia, the non-sustained arrhythmia frequency threshold can be 2-5 episodes per day. Other frequency threshold values may be selected based on patient status or medical history.

In an example, the trigger event detector 222 may detect, or receive from the patient or a clinician, information about an initiation of medication or a therapy, or a change of medication or therapy in the patient. As stated above, certain medication may cause changes in QT interval. The LQTS detector 221 may be triggered to measure QT intervals and to assess QT prolongation in response to an initiation or change of medication or other treatments the patient has received.

In another example, the trigger event detector 222 may detect a physical activity level or a posture of the patient, such as detected by the sensor circuit 210 via one or more sensors (e.g., an accelerometer sensor). Certain postures or activities may more likely trigger QT interval prolongation than other postures or activities. Additionally, information about physical activities or postures may be predictive of the quality of the cardiac signal (e.g., S-ECG) from which the QT intervals are measured. In an example, the LQTS detector 221 may be triggered to measure QT intervals and assess QT prolongation when the trigger event detector 222 detects a low level of physical activity, a sitting posture, or lying down posture. Such activities or postures generally correspond to less motion artifacts or noise in the S-ECG signal. A higher S-ECG signal quality may help improve the accuracy of QT interval measurement and LQTS diagnosis.

The trending circuit 223 can generate a QT interval trend including a plurality of QT intervals at respective times. The QT interval trend indicates how the QT interval progresses with time. Compared to QT or QTc values, a QT interval trend may have additional predictive power for identifying patient risk of LQTS, fatal arrhythmias, or sudden cardiac death. In an example, the trending circuit 223 may generate the QT time interval trend under different postures or physical activities. Indications of QT prolongation can be determined respectively at different postures or physical activities. In another example, the trending circuit 223 can generate the QT interval trend during a course of treatment (e.g., drug therapy or device therapy). QT prolongation may be evaluated continuously or intermittently at different phases of treatment or at different medication doses.

The indication of QT prolongation determined by the LQTS detector 221, and optionally the QT interval trend under different patient conditions or corresponding to different medical events determined by the trending circuit 223, may be used to adjust device operation, such as via one or more of the storage controller 224 or the sensing controller 225. The storage controller 224 can control a memory 230 to store the physiological information acquired from the patient (e.g., the S-ECG signal) in response to a detection of the indication of QT prolongation. In an example, the storage controller 224 may dynamically adjust the size of memory space of a memory 230 allocated for storing the physiological information (e.g., the S-ECG). The size of the allocated memory space may be based on the types of the triggering event detected or received by the trigger event detector 222. For example, if the detected QT prolongation is associated with frequent non-sustained cardiac arrhythmia episodes, then the storage controller 224 can increase the size of an onset buffer for storing a longer period of S-ECG in the memory 230. In some examples, portions of the S-ECG prior to the onset of a non-sustained cardiac arrhythmia episode can be stored in the memory 230. Such stored pre-onset data can be helpful for clinicians to review and adjudicate QT prolongation, perform offline data analysis, and provide diagnosis and other clinical decisions.

The sensing controller 225 can adjust a cardiac sensing parameter based on the detected indication of QT prolongation. By way of example and not limitation, the cardiac sensing parameter being adjusted can include a post-ventricular event refractory period, during which the sensing circuitry (e.g., a sense amplifier) temporarily suspends cardiac event sensing. In an example, such a refractory period may be used to prevent or reduce oversensing of T waves. To mitigate the increased risk of T wave oversensing due to QT prolongation, the sensing controller 225 can extend the post-ventricular event refractory period by an amount based on the detected indication of QT prolongation. In some examples, the adjustment of the cardiac sensing parameter can further be based on QT time interval trend. For example, the post-ventricular event refractory period can be extended if the trending circuit 223 detects an increase trend of QT intervals, or be shortened or be maintained at a default value if a decrease QT interval trend is detected.

In some examples, the sensing controller 225 can adjust the cardiac sensing parameter in one or more devices separate from but communicatively coupled to the device where the controller circuit 220 resides. For example, the controller circuit 220 may be included in a first ambulatory medical device (e.g., a subcutaneously implanted cardiac monitor device). The first ambulatory medical device can transmit a control signal to a second medical device (e.g., an implantable cardiac pacemaker/defibrillator) separated from the first ambulatory medical device via a wired or wireless communication link. The control signal can direct the sensing circuitry of the second medical device to adjust a cardiac sensing parameter, such as extending a post-ventricular event refractory period to avoid or reduce oversensing of cardiac events.

The user interface 240 may include an input unit and an output unit. In an example, at least a portion of the user interface unit 240 may be implemented in the external system 125. The input unit may include a keyboard, on-screen keyboard, mouse, trackball, touchpad, touch-screen, or other pointing or navigating devices. The input unit may enable a system user to program the parameters used for sensing the physiological signals, detecting Q wave and T wave from an S-ECG, detecting and indication of QT prolongation, among others. In an example, the input unit may receive user input of programmable QT or QTc threshold values, or a programmable margin threshold value for the difference between a measured QT interval and a baseline QT interval.

The output unit of the user interface 240 may include a display to display the cardiac signals and the QT intervals measured from the cardiac signal. In an example, the output unit can display a QT (or QTc) interval trend along with events occurred during the trending period, such as patient activity levels, postures, medication use or change of medication, development of a new medical condition, new treatment received or change of treatment, etc. An example of a portion of the QTc being displayed on the display is discussed below with reference to FIGS. 4A-4B. The output unit may include a printer for printing hard copies of the detection information. The information may be presented in a table, a chart, a diagram, or any other types of textual, tabular, or graphical presentation formats. The presentation of the output information may include audio or other media format to alert the system user of the detected arrhythmic events. In an example, the output unit may generate alerts, alarms, emergency calls, or other forms of warnings to signal the system user about the detected QT prolongation. In an example, the output unit may display at least a portion of the stored S-ECG signal corresponding to the detected QT prolongation, and the input unit may receive a user input to confirm, reject, or modify the detected indication of QT prolongation.

The optional therapy circuit 250 may be configured to deliver a therapy to the patient in response to the detected QT prolongation. Examples of the therapy may include electrostimulation therapy delivered to the heart, a nerve tissue, other target tissues, a cardioversion therapy, a defibrillation therapy, or drug therapy. In some examples, the therapy circuit 250 may modify an existing therapy, such as adjust a stimulation parameter or drug dosage.

Components of the system 200 may be implemented in different devices, such as an ambulatory medical device (e.g., the AMD 110A, the insertable medical device 110B, or a wearable ECG recorder such as the body sensor 141) and one or more devices of an external system (e.g., external device 120 or remote device 124 of external system 125). In an example, the sensor circuit 210 may be included in the ambulatory medical device, while the controller circuit 220, the memory 230, and the user interface 240 may be included in an external system. In another example, the ambulatory medical device (e.g., the AMD 110A, the insertable medical device 110B, or a wearable ECG recorder such as the body sensor 141) may include the sensor circuit 210, the controller circuit 220, and the memory 230. The remote device 124 may access the memory 230 to retrieve the stored cardiac signals (e.g., S-ECG) corresponding to the detected QT prolongation, perform further signal analysis to confirm, reject, or modify the indication of QT prolongation and the LQTS diagnosis.

FIGS. 3A-3B illustrate an example of ensemble averaging of a plurality of S-ECG segments 310 and determining a QT interval from a representative S-ECG segment 320. The plurality of S-ECG segments 310, as shown in FIG. 3A, are extracted from the same S-ECG signal over multiple cardiac cycles, and aligned with respect to their respective R wave peaks 312. The length of the S-ECG segments can be user programmable. In this example, the S-ECG segments have the same duration, each comprising four hundred data samples centered at respective R wave peaks. The onset of Q wave and the end of T wave are expected to fall within the the 400-sample S-ECG segment centered at the R wave peak. In an example, the length of the S-ECG segment can be determined based on the heart rate, such that shorter S-ECG segments are selected at faster heart rates (or equivalently shorter cardiac cycles).

The representative S-ECG segment 320, as shown in FIG. 3B, can be computed as the ensemble average of the plurality of S-ECG segments 310 aligned with respect to respective R wave peaks, such that each data value of the representative S-ECG segment 320 at time instant T is computed as an average value of the samples of the plurality of S-ECG segments 310 at the same time instant T. In some examples, other central tendency measures (e.g., a median or a mode) or statistics may be used to determine the representative S-ECG segment 320.

The LQTS detector 221 can detect Q wave onset 324 as the beginning of a downward deflection on the representative S-ECG. The LQTS detector 221 can detect the T wave peak using amplitude thresholding in a detection window following the QRS complex, and detect the T wave end 326 as a turning point, following the T wave peak, that goes upward towards the isoelectric baseline. In some examples, to ensure accurate detections of Q wave onset 324 and T wave end 326, the plurality of S-ECG segments 310 can be screened against a specific signal quality criterion, such as signal-to-noise ratio (SNR) threshold. Only those S-ECG segments satisfying the signal quality criterion are included for computing an ensemble average and determining the representative S-ECG segment 320. The LQTS detector 221 can measure the QT interval 328 from the Q wave onset 324 to the T wave end 326, and detect an indication of QT prolongation using the measured QT time interval and a programmable threshold.

FIG. 4A-4B illustrates by way of example and not limitation a user interface that displays a heart rate-corrected QT (QTc) interval trend along with events occurred during the trending process. FIG. 4A shows a portion of a QTc interval trend 410, along with a marker 412 indicating the time at which the medication is administered, and a marker 414 indicating the time at which the medication dose is changed. FIG. 4B shows a portion of a QTc trend 420, along with markers or annotations indicating patient postures during which the QTc is trended, including, for example, standing 422, sitting 424, and lying down 426. Associating information of clinical events or patient activities with the QT interval trend can help the user (e.g., clinician) quickly identify effects of such events on the QT, alert the user to take timely and necessary interventions, such as adjusting medication or alerting the patient to take precautions to avoid adverse events (e.g., faint or arrhythmia). Also shown in the FIGS. 4A and 4B are programmable QTc thresholds 418 and 428, respectively. A user may use an input device, such as a user-interface (UI) control element 401, to increase (by moving upward) or decrease (by moving downward) the respective QTc thresholds 418 or 428. Other UI control elements (e.g., a slider) may be used to adjust the QTc threshold. Such an adjustable or programmable QTc threshold may allow the user to control the alerts or notification of suspected LQTS diagnosis, such as produced by the output unit of the user interface 240.

FIG. 5 is a flow diagram illustrating an example of a method 500 for detecting an indication of QT prolongation, and adjusting device operation based on the indication of QT prolongation. The method 500 may be implemented and executed in an ambulatory medical device such as an implantable or wearable medical device, or in a remote patient management system. In an example, the method 500 may be implemented in and executed by the physiologic event detector circuit 160 of the AMD 110A, the insertable medical device 110B, the external system 125, or the arrhythmia detection system 200.

The method 500 commences at 510, where a subcutaneous cardiac signal sensed from the patient may be received. An example of the subcutaneous cardiac signal includes a subcutaneous ECG (S-ECG) sensed using one or more subcutaneously implanted electrodes. In some examples, the electrodes for sensing the S-ECG may be included in an implantable cardiac monitor (ICM) device configured for subcutaneous implantation. In some examples, other physiological signals may be sensed from a sensor associated with a patient, or be retrieved from a storage device (e.g., an electronic medical record system) that stores physiological signals recorded from a patient. Examples of such physiological signals may include thoracic or cardiac impedance signal, arterial pressure signal, pulmonary artery pressure signal, left atrial pressure signal, RV pressure signal, LV coronary pressure signal, heart sounds or endocardial acceleration signal, physiologic response to activity, apnea hypopnea index, one or more respiration signals such as a respiration rate signal or a tidal volume signal, among others. The sensed physiological signal may be pre-processed, including one or more of signal amplification, digitization, filtering, or other signal conditioning operations.

At 520, a QT interval can be measured from the subcutaneous cardiac signal, such as using the LQTS detector 221. A representative S-ECG segment can be generated from an ensemble of a plurality of segments of S-ECG during multiple cardiac cycles. From the representative S-ECG segment, Q wave and T wave may be detected, and the QT interval can be measured as a time interval from the onset point of Q wave to the end of T wave.

At 530, an indication of QT prolongation may be detected using the using the measured QT interval and a programmable threshold. The QT detection threshold can be programmed based on age, gender, health status, or medical conditions of the patient. In some examples, measured QT intervals can be corrected for heart rates of the patient, such as by normalizing the measured QT interval with respect to a square-root of the RR interval. Other heart rate-based correction formula may be used. An indication of QT prolongation is detected if the heart rate-corrected QT (QTc) interval exceeds a programmable threshold. By way of example and not limitation, the QTc threshold can be programmed to approximately 500 msec. In some examples, an indication of QT prolongation may be detected the measured QT interval (or the QTc interval) deviates from a baseline QT interval (or a baseline QTc) by an amount exceeding a programmable margin. By way of example and not limitation, the margin threshold can be programmed to approximately 60 msec.

In some examples, QT interval measurement and QT prolongation assessment may be initiated in response to a triggering event, such as a specific type of cardiac arrhythmia. In an example, the triggering event can include frequent non-sustained arrhythmia episodes exceeding a frequency threshold. Frequent non-sustained arrhythmia episodes can be predictive or indicative of LQTS. In an example, the triggering event can include a physical activity level or a posture of the patient. In some examples, measurement of QT interval and detection of QT prolongation may be triggered by an initiation of a therapy or a change of therapy, such as medication or device therapies.

At 540, an alert about the detection of QT prolongation may be provided to a user (e.g., a clinician). The alert may be in a form of a Web page update, phone or pager call, E-mail, SMS, text, or "Instant" message, as well as a message to the patient and a simultaneous direct notification to emergency services and to the clinician. Other alert notifications are possible.

At 550, one or mor device operation may be adjusted in response to the indication of QT prolongation, or optionally a QT interval trend under different patient conditions or corresponding to different medical events (such as determined by the trending circuit 223). In an example, physiological information acquired from the patient (e.g., the S-ECG signal) may be stored in a memory device in response to a detection of the indication of QT prolongation.

In an example, the size of memory space allocated for storing the physiological information (e.g., the S-ECG) may be dynamically adjusted based on the types of the triggering event. For example, if the detected QT prolongation is associated with frequent non-sustained cardiac arrhythmia episodes, then the size of an onset buffer may be increased to store a longer period of S-ECG in the memory. In some examples, a cardiac sensing parameter may be adjusted based on the detected indication of QT prolongation. For example, a post-ventricular event refractory period can be extended to prevent or reduce oversensing of T waves. In some examples, the adjustment of the cardiac sensing parameter can further be based on QT time interval trend. For example, the post-ventricular event refractory period can be extended an increase QT interval trend is detected, or be shortened or be maintained at a default value if a decrease QT interval trend is detected. In some examples, the cardiac sensing parameter (such as a post-ventricular event refractory period) in one or more devices separate from but communicatively coupled to the device that detects the QT prolongation can be adjusted. For example, the indication of QT prolongation is detected by a first ambulatory medical device (e.g., a subcutaneously implanted cardiac monitor device). The first ambulatory medical device can transmit a control signal to a second medical device (e.g., an implantable cardiac pacemaker/defibrillator) separated from the first ambulatory medical device, and direct the second medical device to adjust a cardiac sensing parameter therein.

In some examples, the method 500 may include the optional step of delivering a therapy to the patient in response to the detection of the cardiac arrhythmia, such as via the optional therapy circuit 250 as illustrated in FIG. 2. Examples of the therapy may include electrostimulation therapy delivered to the heart, a nerve tissue, other target tissues, a cardioversion therapy, a defibrillation therapy, or drug therapy including delivering drug to a tissue or organ. In some examples, an existing therapy or treatment plan may be modified to treat the detected arrhythmia, such as modify patient follow-up schedule, or adjust a stimulation parameter or drug dosage.

FIG. 6 illustrates generally a block diagram of an example machine 600 upon which any one or more of the techniques (e.g., methodologies) discussed herein may perform. Portions of this description may apply to the computing framework of various portions of the AMD 110A, the insertable medical device 110B, a wearable sensor device such as included in the sensor devices 140, or the external system 125.

In alternative embodiments, the machine 600 may operate as a standalone device or may be connected (e.g., networked) to other machines. In a networked deployment, the machine 600 may operate in the capacity of a server machine, a client machine, or both in server-client network environments. In an example, the machine 600 may act as a peer machine in peer-to-peer (P2P) (or other distributed) network environment. The machine 600 may be a personal computer (PC), a tablet PC, a set-top box (STB), a personal digital assistant (PDA), a mobile telephone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein, such as cloud computing, software as a service (SaaS), other computer cluster configurations.

Examples, as described herein, may include, or may operate by, logic or a number of components, or mechanisms. Circuit sets are a collection of circuits implemented in tangible entities that include hardware (e.g., simple circuits, gates, logic, etc.). Circuit set membership may be flexible over time and underlying hardware variability. Circuit sets include members that may, alone or in combination, perform specified operations when operating. In an example, hardware of the circuit set may be immutably designed to carry out a specific operation (e.g., hardwired). In an example, the hardware of the circuit set may include variably connected physical components (e.g., execution units, transistors, simple circuits, etc.) including a computer readable medium physically modified (e.g., magnetically, electrically, moveable placement of invariant massed particles, etc.) to encode instructions of the specific operation. In connecting the physical components, the underlying electrical properties of a hardware constituent are changed, for example, from an insulator to a conductor or vice versa. The instructions enable embedded hardware (e.g., the execution units or a loading mechanism) to create members of the circuit set in hardware via the variable connections to carry out portions of the specific operation when in operation. Accordingly, the computer readable medium is communicatively coupled to the other components of the circuit set member when the device is operating. In an example, any of the physical components may be used in more than one member of more than one circuit set. For example, under operation, execution units may be used in a first circuit of a first circuit set at one point in time and reused by a second circuit in the first circuit set, or by a third circuit in a second circuit set at a different time.

Machine (e.g., computer system) 600 may include a hardware processor 602 (e.g., a central processing unit (CPU), a graphics processing unit (GPU), a hardware processor core, or any combination thereof), a main memory 604 and a static memory 606, some or all of which may communicate with each other via an interlink (e.g., bus) 608. The machine 600 may further include a display unit 610 (e.g., a raster display, vector display, holographic display, etc.), an alphanumeric input device 612 (e.g., a keyboard), and a user interface (UI) navigation device 614 (e.g., a mouse). In an example, the display unit 610, input device 612 and UI navigation device 614 may be a touch screen display. The machine 600 may additionally include a storage device (e.g., drive unit) 616, a signal generation device 618 (e.g., a speaker), a network interface device 620, and one or more sensors 621, such as a global positioning system (GPS) sensor, compass, accelerometer, or other sensor. The machine 600 may include an output controller 628, such as a serial (e.g., universal serial bus (USB), parallel, or other wired or wireless (e.g., infrared (IR), near field communication (NFC), etc.) connection to communicate or control one or more peripheral devices (e.g., a printer, card reader, etc.).

The storage device 616 may include a machine readable medium 622 on which is stored one or more sets of data structures or instructions 624 (e.g., software) embodying or utilized by any one or more of the techniques or functions described herein. The instructions 624 may also reside, completely or at least partially, within the main memory 604, within static memory 606, or within the hardware processor 602 during execution thereof by the machine 600. In an example, one or any combination of the hardware processor

602, the main memory 604, the static memory 606, or the storage device 616 may constitute machine-readable media.

While the machine-readable medium 622 is illustrated as a single medium, the term "machine readable medium" may include a single medium or multiple media (e.g., a centralized or distributed database, and/or associated caches and servers) configured to store the one or more instructions 624.

The term "machine readable medium" may include any medium that is capable of storing, encoding, or carrying instructions for execution by the machine 600 and that cause the machine 600 to perform any one or more of the techniques of the present disclosure, or that is capable of storing, encoding or carrying data structures used by or associated with such instructions. Non-limiting machine-readable medium examples may include solid-state memories, and optical and magnetic media. In an example, a massed machine-readable medium comprises a machine readable medium with a plurality of particles having invariant (e.g., rest) mass. Accordingly, massed machine-readable media are not transitory propagating signals. Specific examples of massed machine-readable media may include: non-volatile memory, such as semiconductor memory devices (e.g., Electrically Programmable Read-Only Memory (EPROM), Electrically Erasable Programmable Read-Only Memory (EEPROM)) and flash memory devices; magnetic disks, such as internal hard disks and removable disks; magneto-optical disks; and CD-ROM and DVD-ROM disks.

The instructions 624 may further be transmitted or received over a communications network 626 using a transmission medium via the network interface device 620 utilizing any one of a number of transfer protocols (e.g., frame relay, internet protocol (IP), transmission control protocol (TCP), user datagram protocol (UDP), hypertext transfer protocol (HTTP), etc.). Example communication networks may include a local area network (LAN), a wide area network (WAN), a packet data network (e.g., the Internet), mobile telephone networks (e.g., cellular networks), Plain Old Telephone (POTS) networks, and wireless data networks (e.g., Institute of Electrical and Electronics Engineers (IEEE) 802.11 family of standards known as WiFi®, IEEE 802.16 family of standards known as WiMax®), IEEE 802.15.4 family of standards, peer-to-peer (P2P) networks, among others. In an example, the network interface device 620 may include one or more physical jacks (e.g., Ethernet, coaxial, or phone jacks) or one or more antennas to connect to the communications network 626. In an example, the network interface device 620 may include a plurality of antennas to wirelessly communicate using at least one of single-input multiple-output (SIMO), multiple-input multiple-output (MIMO), or multiple-input single-output (MISO) techniques. The term "transmission medium" shall be taken to include any intangible medium that is capable of storing, encoding or carrying instructions for execution by the machine 600, and includes digital or analog communications signals or other intangible medium to facilitate communication of such software.

Various embodiments are illustrated in the figures above. One or more features from one or more of these embodiments may be combined to form other embodiments.

The method examples described herein can be machine or computer-implemented at least in part. Some examples may include a computer-readable medium or machine-readable medium encoded with instructions operable to configure an electronic device or system to perform methods as described in the above examples. An implementation of such methods may include code, such as microcode, assembly language code, a higher-level language code, or the like. Such code may include computer readable instructions for performing various methods. The code can form portions of computer program products. Further, the code can be tangibly stored on one or more volatile or non-volatile computer-readable media during execution or at other times.

The above detailed description is intended to be illustrative, and not restrictive. The scope of the disclosure should, therefore, be determined with references to the appended claims, along with the full scope of equivalents to which such claims are entitled.

What is claimed is:

1. A medical-device system for monitoring a patient, comprising:
   a controller circuit, including a long QT syndrome (LQTS) detector configured to:
      receive a subcutaneous cardiac signal sensed from the patient;
      measure a Q wave-to-T wave (QT) time interval from the subcutaneous cardiac signal; and
      detect an indication of QT prolongation using the measured QT time interval and a programmable threshold; and
   dynamically adjust a memory space of a memory circuit allocated for storing the subcutaneous cardiac signal based on a type of cardiac event detected from the patient or the detected indication of QT prolongation.

2. The medical-device system of claim 1, comprising a sensing circuit configured to sense the subcutaneous cardiac signal including a subcutaneous electrocardiogram (S-ECG) via one or more subcutaneously implanted electrodes in the patient.

3. The medical-device system of claim 2, wherein the LQTS detector is configured to generate a representative S-ECG segment from an ensemble of segments of the S-ECG in multiple cardiac cycles, and to measure the QT time interval using the representative S-ECG.

4. The medical-device system of claim 1, wherein:
   the LQTS detector is configured to generate a QT time interval trend under different postures or physical activities of the patient, and to detect the indication of QT prolongation at different postures or physical activities; and
   an output unit configured to display the QT time interval trend and the indication of QT prolongation at the different postures or physical activities.

5. The medical-device system of claim 1, wherein:
   the LQTS detector is configured to generate a QT time interval trend during a course of treatment of the patient, and to detect the indication of QT prolongation during the course of treatment; and
   an output unit configured to display the QT time interval trend and the indication of QT prolongation during the course of treatment.

6. The medical-device system of claim 1, wherein the LQTS detector is configured to measure the QT time interval and to detect the indication of QT prolongation in response to cardiac arrhythmia, or frequent non-sustained arrhythmia episodes exceeding a frequency threshold.

7. The medical-device system of claim 1, wherein the LQTS detector is configured to measure the QT time interval and to detect the indication of QT prolongation at a specific posture state.

8. The medical-device system of claim 1, wherein the LQTS detector is configured to measure the QT time interval and to detect the indication of QT prolongation in response to an initiation of a therapy or a change of therapy.

9. The medical-device system of claim 1, comprising the memory circuit configured to store at least a portion of the subcutaneous cardiac signal in response to the indication of QT prolongation.

10. The medical-device system of claim 1, comprising a first ambulatory medical device operatively in communication with a second medical device separated from the first ambulatory medical device,
   wherein the first ambulatory medical device includes the controller circuit configured to communicate a control signal to the second medical device to adjust a cardiac sensing parameter of the second medical device.

11. The medical-device system of claim 1, wherein the controller circuit is configured to dynamically adjust a size of an onset buffer to store a longer period of the subcutaneous cardiac signal sensed from the patient in the memory circuit based on the detected indication of QT prolongation.

12. The medical-device system of claim 11, wherein the LQTS detector is configured to generate an ensemble average subcutaneous cardiac signal using the subcutaneous cardiac signal in the dynamically adjusted onset buffer and to measure the QT time interval using the ensemble average subcutaneous cardiac signal in the dynamically adjusted onset buffer.

13. The medical-device system of claim 1, comprising:
   a user interface configured to receive a user input of the programmable threshold, the user interface including an output unit configured to generate a programmable alert of the detected indication of QT prolongation corresponding to the user input of the programmable threshold.

14. A method for monitoring a patient, comprising:
   receiving a subcutaneous cardiac signal sensed from the patient;
   measuring, via a controller circuit, a Q wave-to-T wave (QT) time interval from the subcutaneous cardiac signal;
   detecting, via the controller circuit, an indication of QT prolongation using the measured QT time interval and a programmable threshold; and
   dynamically adjusting a memory space of a memory circuit allocated for storing the subcutaneous cardiac signal based on a type of cardiac event detected from the patient or the detected indication of QT prolongation.

15. The method of claim 14, wherein the subcutaneous cardiac signal includes a subcutaneous electrocardiogram (S-ECG) sensed using one or more subcutaneously implanted electrodes in the patient, the method comprising:
   generating a representative S-ECG segment from an ensemble of segments of the S-ECG in multiple cardiac cycles; and
   measuring the QT time interval using the representative S-ECG.

16. The method of claim 14, wherein measuring the QT interval and detecting the QT prolongation is triggered by one or more triggering events including:
   a cardiac arrhythmia;
   frequent non-sustained arrhythmia episodes;
   a specific posture state; or
   an initiation of a therapy or a change of therapy.

17. The method of claim 14, comprising:
   storing at least a portion of the subcutaneous cardiac signal in response to the indication of QT prolongation.

18. The method of claim 14, wherein the indication of QT prolongation is detected by a first ambulatory medical device, the method comprising:

communicating a control signal from the first ambulatory medical device to a second medical device separated from and communicatively coupled to the first ambulatory medical device; and adjusting a cardiac sensing parameter of the second medical device.

19. A medical-device system for monitoring a patient, comprising:

a controller circuit, including a long QT syndrome (LQTS) detector configured to:

receive a subcutaneous cardiac signal sensed from the patient;

measure a Q wave-to-T wave (QT) time interval from the subcutaneous cardiac signal; and detect an indication of QT prolongation using the measured QT time interval and a programmable threshold; and adjust a cardiac sensing parameter based on the indication of QT prolongation, including to extend a post-ventricular event refractory period by an amount based on the detected indication of QT prolongation.

20. The medical-device system of claim 19, comprising:

a user interface configured to receive a user input of the programmable threshold, the user interface including an output unit configured to generate a programmable alert of the detected indication of QT prolongation corresponding to the user input of the programmable threshold, wherein the controller circuit is configured to dynamically adjust a memory space of a memory circuit allocated for storing the subcutaneous cardiac signal based on a type of cardiac event detected from the patient or the detected indication of QT prolongation.

* * * * *